United States Patent [19]

Cunningham

[11] Patent Number: 4,535,620
[45] Date of Patent: Aug. 20, 1985

[54] METHOD FOR AUTOMATICALLY MEASURING THE AMOUNT OF WATER IN A NATURAL GAS PIPELINE WITH THE AID OF A COMPUTER CONTROLLED GAS CHROMATOGRAPH

[75] Inventor: Richard D. Cunningham, Omaha, Nebr.

[73] Assignee: InterNorth, Inc., Omaha, Nebr.

[21] Appl. No.: 522,791

[22] Filed: Aug. 12, 1983

[51] Int. Cl.³ ............................................. G01N 31/08
[52] U.S. Cl. ..................................................... 73/23.1
[58] Field of Search ........................... 73/23.1; 422/89; 436/139, 161

[56] References Cited

U.S. PATENT DOCUMENTS 3,714,812  2/1973  Drinkwater et al. ................. 73/23.1

OTHER PUBLICATIONS

J. E. Lovelock, "Electron Absorption Detectors and Tech. for Use in Quan. and Qual. Anal. by Gas Chrom.", *Anal. Chem.*, vol. 35, No. 4, pp. 474–481, Apr. 1963.

D. H. Fuller, "Gas Chrom. in Plant Streams", *ISA Journal*, pp. 440–444, Nov. 1956.

J. A. Favre et al., "How Phillips Applies Chrom.", *Petroleum Refiner*, vol. 37, No. 11, pp. 251–254, Nov. 1958.

R. F. Wall et al., "Process Control by Gas Chrom. in Chem. Industry", *Annals N.Y. Acad. of Sci.*, 72, (13), pp. 739–750, Mar. 20, 1959.

*Primary Examiner*—Stephen A. Kreitman
*Attorney, Agent, or Firm*—Zarley, McKee, Thomte, Voorhees & Sease

[57] ABSTRACT

A method for analyzing various components in a natural gas pipeline with the aid of a computer controlled gas chromatograph comprising the steps of: (a) providing the computer control unit with a data base for operating the gas chromatograph including at least: (1) periodically causing a sample of the natural gas to be supplied to the gas chromatograph; (2) operating the gas chromatograph to analyze the various components in the natural gas stream; (3) computing the amount of the various components in the natural gas stream; and (4) reporting the amount of components in the natural gas stream.

1 Claim, 3 Drawing Figures

METHOD FOR AUTOMATICALLY MEASURING THE AMOUNT OF WATER IN A NATURAL GAS PIPELINE WITH THE AID OF A COMPUTER CONTROLLED GAS CHROMATOGRAPH

BACKGROUND OF THE INVENTION

This invention relates to a method for automatically measuring the amount of water in a natural gas stream through the use of a gas chromatograph which is controlled and operated by a computer control unit.

The prior art is replete with devices and methods for the detection and measurement of water, none of which is applicable to the problem of detection and measurement of low water levels in gaseous hydrocarbons flowing in a pipeline. One such device is an infrared absorption type hygrometer. This device takes advantage of the fact that water absorbs electromagnetic radiation in the infrared region, specifically radiation of 1.40 to 1.93 microns in wave length. By measuring the attenuation or decrease in light intensity of a beam of this wave length as it passes through a gas, the moisture content of the sample can be determined. This device is not sensitive enough to detect minute quantities of water and is subject to error caused by interference from any other compounds that absorb radiation in the same wave lenght range. These factors make it unsuitable for use in the present application.

Another type of water measurement device is a conductivity cell. This device is an acid conductivity cell wherein the electrical conductivity of an insulating material coated with sulfuric acid is measured in the environment of varying moisture content. In theory, the conductivity of the cell has a direct correspondence to the water level, and the acid coating on the insulating material becomes more conductive when more water molecules are present on its surface. This device gives a large variation of moisture level readings with changes in ambient temperature. Also, when subjected to either a dry gas flow or to a liquid hydrocarbon, the conductivity of the cell decays rapidly.

Another moisture measurement device is an electrolytic hygrometer. This device employs a hygroscopic salt, such as phosphorous pentoxide, to absorb moisture from a fluid sample and subsequently to perform an electrolysis of water into hydrogen and oxygen. The electrolysis current required is a measure of the amount of moisture present. There are a number of materials that will create problems if they are present in the fluid sample. A phenomenon called the "recombination effect" introduces large errors at low moisture levels in hydrogen-rich or oxygen-rich samples. This instrument is also unstable in the presence of unsaturated monomers, alcohols, amines, ammonia and hydrogen fluoride. Alcohols are seen by the cell as water, and the amines and ammonia react with the desiccant which is used to absorb the moisture.

Still another commercial measurement device is known as the piezoelectric hygrometer. It utilizes twin piezoelectric crystals coated with a hygroscopic material. Water from the fluid sample is absorbed by the crystal coating, increasing the total mass and decreasing the oscillating frequency of the crystal. The moisture level is determined by comparing the frequency of the crystal exposed to the sample gas with one exposed to bone-dry gas. Any liquid present in the sample may be forced into the crystal cell, thereby immediately stopping crystal oscillation. Water will ruin the crystal coating instantly while other solvents may soften the crystal coating and ruin the calibration of the instrument. In addition, such monomers as butadiene and styrene may polymerize and coat the crystals, thus preventing proper operation of the unit. This unit is commonly used to monitor water concentration in natural gas, but because of these problems, it gives unreliable measurements.

Yet another commercially used device is the impedence-type hygrometer, an instrument capable of measuring a wide range of moisture levels. This instrument measure water content of a sample by means of a probe whose electrical impedance is a function of the vapor pressure of the moisture in the fluid. A typical sensor is constructed of porous aluminum oxide. Since the pore wall openings are small in relation to organic molecules, admission into the pore cavity is limited to small molecules such as water. The aluminum oxide sensor is sensitive to water vapor pressure and is, therefore, not affected by large concentrations of petroleum gases, freons, hydrogen sulfide, ozone or sulfur dioxide. Unfortunately, this sensor is affected by polar substances other than water, such as ammonia, methyl amines, and alcohols. The common presence of these materials in pipeline hydrocarbons renders the impedence-type hygrometer unusable in the present application.

The mirror dew point apparatus is still another type of device which has been used to measure the dew point of gas streams. The apparatus consists of a pressure cell containing a highly polished mirror which can be cooled by some common refrigerant, such as propane. A gas stream is passed over the mirror at a convenient pressure, and the temperature of the mirror is slowly reduced until visible condensation occurs. The water content of the gas stream can be determined from established tables by observing the temperature and pressure. This method is listed in the 1969 *Book of ASTM Standards, Part* 19. It is noted in this text that some gaseous fuels contain vapors of hydrocarbons or other components that easily condense into liquid and sometimes interfere with or mask the water dew point. This method, although it is an ASTM standard, can give questionable results if the dew point of the condensable hydrocarbons is higher than that of the water vapor and those hydrocarbons that are present in large amounts.

If that is the case, these hydrocarbons may flood the mirror and obscure or wash off the water dew point. This condition is especially true for propane and heavier hydrocarbons when water vapor content is quite low, as is the case in natural gas pipelines.

One method that works quite well is the Bureau of Standards Gravimetric Procedure. This method is the primary standard for calibration of all types of gas or moisture analyzers. It employs two water-absorbant materials, magnesium perchlorate and phosphorus pentoxide, to absorb all of the moisture in a specific volume of gas samples. The drying tubes containing the absorbant materials or desiccants are very carefully weighed before and after the gas sample is passed through them. The weight gain is the water which has been absorbed from the sample. This method is extremely accurate, but there are several significant measurement technique problems which render this method unusable for measuring water content at various locations along the length of a pipeline. The handling of the desiccant tubes requires the utmost of care since even fingerprints on the tube's surface will introduce error into the measurements. The desiccants will also absorb other impurities which may be present in the gas sample, thus making this method even more subject to error if it is used at moisture levels in actual pipelines.

Gas chromatographs have long been used to analyze various components in a natural gas stream. However, none of the detectors used had adequate sensitivity for measuring low water levels.

The use of an electron capture detector in connection with a chromatographic column, and tubing made of nonwater-absorbing materials overcomes all of the disadvantages of the prior art devices discussed above. The method of the present invention allows accurate detection and measurement of water at levels well below five parts per million. The development of a highly accurate electron capture device is relatively new. The use of the electron capture detector in gas chromatography is widely used in the analysis of trace quantities of chlorinated hydrocarbons. Highly chlorinated pesticides such as lindane (hexachlorocyclohexane) are detectable at the one picogram level. The electron capture detector is extremely sensitive to water. Response to natural gas hydrocarbons is very low. Some contaminates such as hydrogen sulfide, carbonyl sulfide, and other sulfur compounds are detectable. However, with the proper selection of operating conditions and columns, they do not interfere with water measurement.

SUMMARY OF THE INVENTION

Briefly described, the method of the present invention provides for the detection and measurement of minute quantities of water in natural gas. The method comprises the steps of withdrawing a sample of natural gas, mixing the gas sample with a carrier gas, causing the mixture to flow into a gas chromatographic device, and causing the separated mixture to flow from the gas chromatographic device into an electron capture detector for detection and measurement of the water concentration in the natural gas sample. The gas chromatographic device contains a chromatographic column having a nonvolatile stationary phase present therein for separation of the various components of the gaseous sample. The interior surfaces of the chromatographic column and all other surfaces through which the natural gas sample flows are made from a material which does not absorb water or react react within, and has a very low permeability (atmospheric moisture can permeate through the tubing if its permeability to water is high). Preferably, this material is glass or one of the tetrafluoroethylene polymers. The plastic must have been simultaneously heat conditioned and purged with an inert gas before us to drive off residual fluorocarbons. Glass and these conditioned polymers are inert at the operating conditions of this invention, and they do not absorb or react with even small amounts of water. Stainless steel, on the other hand, will absorb enough water to significantly lower the amount of water reaching the detector. Since the electron capture detector is extremely sensitive to chlorinated hydrocarbons, chlorinated hydrocarbons, even in small concentrations, can permeate through many plastics and cause severe interference. For this reason, the preferred column and tubing material is stainless steel with Teflon tubing inside.

The conventional laboratory method of mixing a gas sample to be analyzed with carrier gas is to withdraw a precise amount of gas with a calibrated syringe and inject it into the carrier gas upstream of the column. For low levels of water, this method will not result in acceptable accuracy. Atmospheric moisture will absorb on the syringe needle and will desorb when it comes into contact with the carrier gas. Atmospheric moisture will also enter at the point where the needle is injected into the carrier gas stream. This method, if applicable, would necessarily involve a tremendous utilization of skilled manpower. The preferred method is to have the gas chromatographic device configured in such a manner that it can be automatically controlled by an electronic controller.

Therefore, it is a principal object of the invention to provide a method for automatically measuring the amount of water in a natural gas stream through the use of a gas chromatograph.

Yet another object of the invention is to provide a method for automatically measuring the amount of water in a natural gas stream through the use of a gas chromatograph which is controlled and operated by a computer control unit.

Yet another object of the invention is to provide a method for automatically measuring the amount of water in a natural gas pipeline which is accurate.

These and other objects will be apparent to those skilled in the art.

DESCRIPTION OF THE PREFERRED EMBODIMENT

Figure 1:
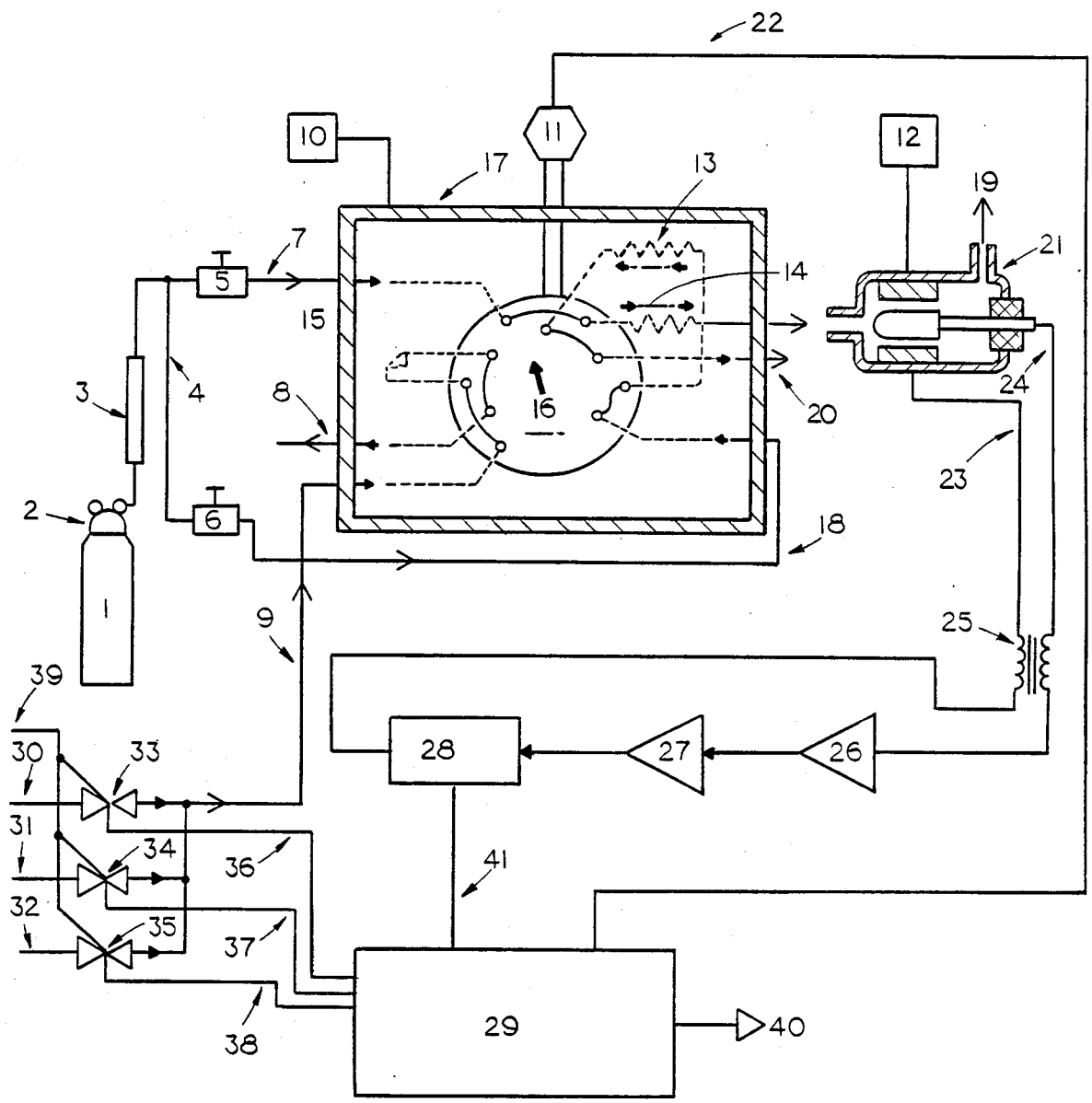
FIG. 1 is schematic view illustrating the apparatus in the "fill position"

Referring to the drawings, the various components thereof are identified as follows:

(1) Carrier gas—Nitrogen or a mixture of 5 percent methane, 95 percent argon—standard commercially available mixture
(2) Pressure regulator—Output pressure 0–100 psig
(3) Active molecular sieve dryer
(4) Stainless steel line—⅛-inch O.D. gas chromatograph grade
(5) Flow controller
(6) Flow controller
(7) Stainless steel line—⅛-inch O.D. G.C. grade
(8) Sample vent line
(9) Sample line—Stainless steel, ⅛-inch O.D. Teflon-lined
(10) Oven temperature controller
(11) Ten Port valve operator
(12) Electron capture cell temperature controller
(13) Stripper column—⅛-inch S.S. Teflon-lined about 6 inches long, filled with 50/50 Porapak N and Porapak QS
(14) Main column—⅛-inch S.S. Teflon-lined about 6 feet long, filled with 50/50 Porapak N and Porapak QS
(15) Sample loop—⅛-inch S.S. Teflon-lined, 6 feet long, internal volume 3.7 cc
(16) Ten Port S.S Valve—Valco #V-10-HPa (this is the only valve that will work in this application)
(17) Heated oven
(18) S.S. line—⅛-inch carrier gas line
(19) Vent line
(20) Vent line

(21) Electron capture detector cell—Hewlett Packard Model 181713A
(22) Ten Port valve operator control line
(23) Wire
(24) Wire
(26) Integrating amplifier
(27) Exponential amplifier
(28) Voltage to frequency converter
(29) Electronic controller—micro-computer
(30) S.S. sample line (calibration gas)
(31) S.S. sample line (natural gas)
(32) S.S. sample line (natural gas)
(33) Three-way Solenoid S.S. valve
(34) Three-way Solenoid S.S. valve
(35) Solenoid control wire from micro-computer
(37) Solenoid control wire from micro-computer
(39) Sample gas vent line
(40) Micro-computer output—Analog meter, digital display, printer, telephone line, master computer, 4 to 20 ma current signal
(41) Signal wire—digital frequency from V/F converter to micro-computer.

Simply defined, gas chromatography is a technique for separating volatile substances by percolating a gas stream over a stationary phase. In this case, the stationary phase is a nonvolatile porous polymer and is a commercially available 50/50 mixture of Porapak ®QS and Porapak ®N. Both of these materials are styrene-divinylbenzene resins that have been treated by a proprietary process. In gas chromatography, the components to be separated are carried through the column by an inert gas. The sample mixture is partitioned in the carrier gas by the nonvolatile stationary phase which is a modified porous polymer as described above. The stationary phase selectively retards the sample components until they form separate bands in the carrier gas. These component bands leave the column in the gas stream and are recorded as a function of time by a detector, which, in the present invention, is an electron capture detector.

The operating principle of the electron capture detector in the chromatograph is basically a measure of the loss of a signal. As the carrier gas (comprised, for example, of 95 percent Argon and 5 percent Methane) flows through the detector, a radioactive Nickel 63 source emits electrons which collide with molecules of the carrier gas resulting in the formation of "slow" electrons. These slow electrons migrate to the anode under a fixed applied voltage called the "cell voltage" which can be a train of modulated pulses applied to the electrode. The pulse frequency is modulated so that the collection of electrons on the anode, which creates a "standing" current, is kept at a constant value. If a sample containing electron absorbing molecules then comes through the detector, the standing current tries to decrease. The electron capture controller senses this decrease and increases the pulse frequency to maintain the standing current. The process of maintaining the standing current then generates the output signal. The output signal is used to provide the measurement of the level of water present in the sample.

This method utilizing the pulse frequency is a relatively new innovation in electron capture detection which results in an output being linearly proportional to sample concentration over a wide dynamic range. The original approach held the frequency constant and used the change in standing current as the output variable, giving a linear output for only small concentrations of a sample.

The electron capture detector is extremely sensitive to water and hydrogen sulfide and virtually insensitive to hydrocarbons, alcohols, and other components normally found in natural gas. The electron capture detector is 100 times less sensitive to hydrocarbons since they do not absorb electrons to any great extent.

MAIN COLUMN AND STRIPPER COLUMN PREPARATION

Mix 10 cc each of Porapak N and Porapak QS. To facilitate mixing, the two polymers are mixed together in a solution of reagent grade methanol. Because of electrostatic changes on the two polymers, they are very difficult to mix dry. After mixing, the container containing the two polymers and methanol is dried for 24 hours in a 200 C. oven. The columns are then packed by conventional methods. The columns are then conditioned for a minimum of 72 hours by simultaneously heating the packed columns to 150 C. and purging them with dry carrier gas. This is done to drive off residual fluorocarbons in the Teflon tubing and to drive off methanol and water in the column packing material.

Figure 2:
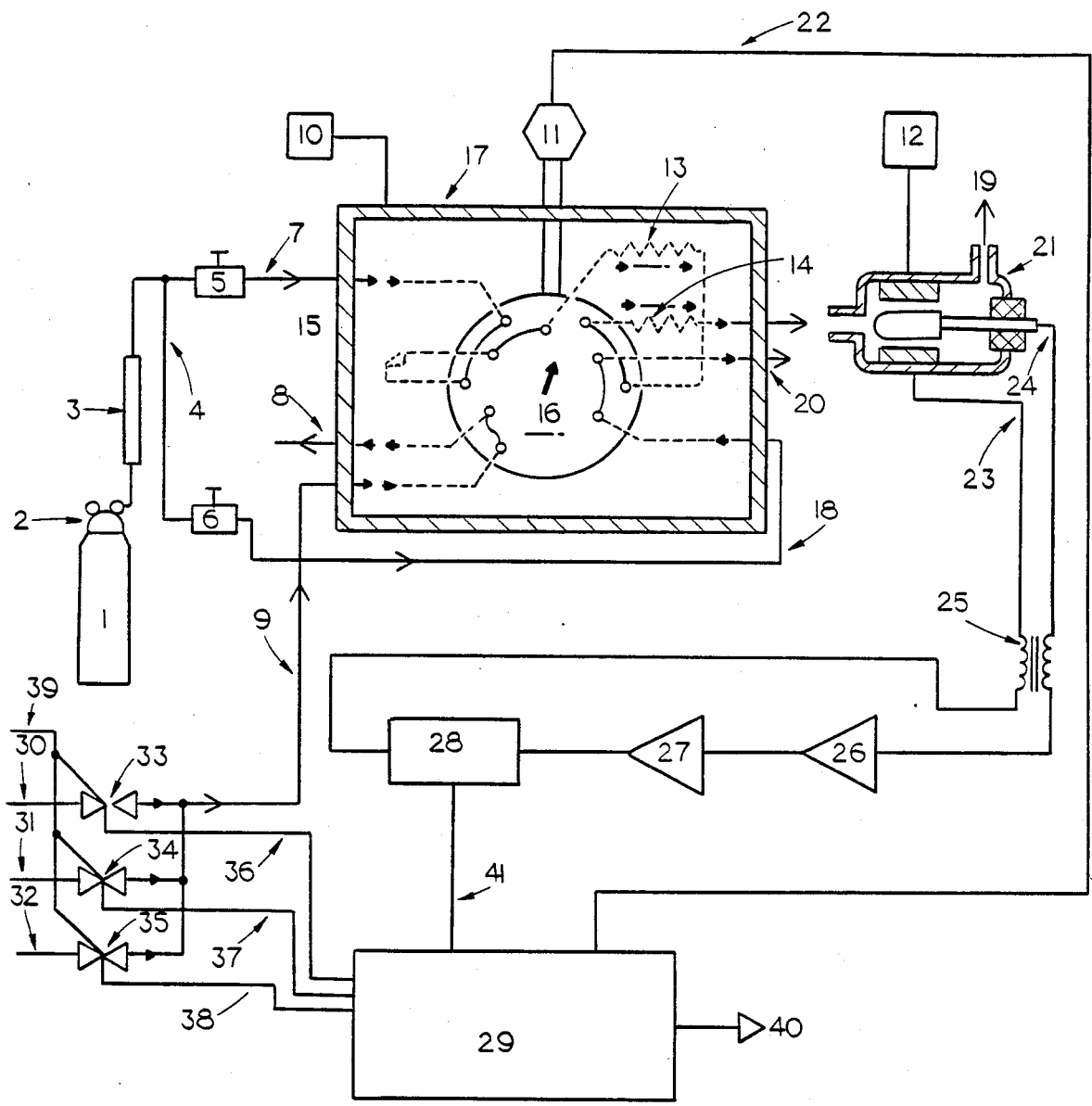
FIG. 2 is a view similar to FIG. 1 except that the apparatus is in the "inject position"

Except for the position of Valve 16, FIG. 1 is identical to FIG. 2. Valve 16 is in the "fill position" in FIG. 1 and in the "inject position" in FIG. 2. Steel high pressure cylinder 1 contains high pressure ultra pure carrier gas which can be either nitrogen or a mixture of 5 percent methane and 95 percent argon. These are standard commercially available gases. Pressure regulator 2 regulates carrier gas pressure to approximately 100 psig. Pressure regulator 2 must be equipped with a diaphragm that is not permeable to atmospheric gases, especially to atmospheric oxygen and moisture. Buna-N and neoprene, common diaphragm materials, cannot be used. A regulator equipped with a stainless steel diaphragm is recommended. Low pressure carrier gas flows through a molecular sieve dryer 3 to remove trace moisture, through line 4 to flow controllers 5 and 6. Oven 17 houses the following:

Ten Port sample valve 16
sample loop 15
stripper column 13
main column 14
vent lines 8 and 20.

Oven temperature is controlled to within ±0.25° C. by temperature controller 10. Valve operator 11 switches Ten Port valve 16 between "fill position" and "inject position." Carrier gas lines 7 and 18 and vent lines 8 and 20 are stainless steel. Sample loop 15, stripper column 13, and main column 14 are approximately 6 feet, 6 inches and 6 feet in length respectively and are Teflon-lined. All lines in, out, and within oven 17 are ideally ⅛-inch O.D.

When Ten Port valve 16 is in "fill position" (FIG. 1), carrier gas enters Ten Port valve 16 and goes directly to main column 14 to flush it out and to establish a base line for electron capture detector 21. Carrier gas flow rate through main column 14 is controlled by flow controller 5. Carrier gas is also back-flushed through stripper column 13 to remove any heavy hydrocarbons or other heavy components which may be contained therein. Carrier gas flow through stripper column 13 is controlled by flow controller 6. Natural gas whose water concentration is to be measured flows through line 9 into Ten Port valve 16, through sample loop 15, back into Ten Port valve 16, and to vent 8.

When Ten Port valve 16 is in "inject position" (FIG. 2), natural gas to be analyzed flows into Ten Port valve 16 and directly back to vent 8. Carrier gas flows into Ten Port valve 16 through sample loop 15, thereby pushing out the gas sample. Gas sample and carrier gas then flows through stripper column 13 where heavy hydrocarbons are slowed down, then flows back to Ten Port valve 16, and finally through main column 14 where water is separated from the lighter compounds and then into electron capture detector 21. Ten Port valve 16 only stays in the "inject position" (FIG. 2) for a short time, approximately ten to twenty-five seconds depending upon the flow rate of the carrier gas. Ten Port valve 16 stays in the "inject position" just long enough for all water to pass through stripper column 13, but before heavy hydrocarbons also start to elute.

Ten Port valve 16 then reverts back to "fill position" (FIG. 1) and carrier gas pushes the gas sample through main column 14 into electron capture detector 21 as main column 14 is separating water from the lighter components of the gas sample. Meanwhile, carrier gas is back-flushed through stripper column 13 to remove heavy hydrocarbons, and another gas sample is flowing through sample loop 15 in preparation for another analysis. Switching of Ten Port valve 16 is done by valve operator 11 which receives a switching signal via control line 22 from micro-computer 29.

The various components bands, as they elute from main column 14, pass through electron capture detector cell 21 and then through vent 19. Temperature controller 12 maintains electron capture detector cell 21 to within $\pm 1°$ C. A train of modulated pulses is applied to electron capture detector 21 via shielded wire 23. Return path at these modulated pulses is through shielded wire 24. Modulated pulses are then integrated by integrating operational amplifier 26. This voltage is linearized by exponentiating amplifier 27 and applied to voltage to frequency converter 28. Current flow through electron capture detector 21 is maintained at $10^{-9}$ amps. A change in component concentration flowing out of main column 14 into electron capture detector 21 causes a change in current flow. This change in current flow causes a decrease or increase in frequency of the pulse train from voltage to frequency converter 28. Thus, through this feedback loop, the $10^{-9}$ amp current is maintained. Voltage to frequency converter 28 also provides a frequency output via shielded cable 14 to micro-computer 29. Change in frequency and time thereof is processed by microcomputer 29 in computing the amount of water in the gas sample. After computing the amount of water in the gas stream, data is output 40. Output 40 can be in any format, such as voltage to analog meter, digital display, printer, telephone line, master computer, or 4 to 20 ma current signal.

Micro-computer 29, via control signal lines 36 or 37, decides which gas sample line 30 or 31 is to anallyzed. Control signal line 36 controls 3-way solenoid valve 33. Control signal line 37 controls 3-way solenoid valve 34. Only one solenoid valve is energized at a time. Gas flows from the energized valve into oven 17 through stainless steel, Teflon-lined tubing 9. Gas from the 3-way solenoid valve that is not energized is by-passed through the valve to vent line 39. Two gas inlet lines 30 and 31 are shown; however, as many as are required can be installed. One of the inlet lines always is calibration gas. The micro-computer 29 is programmed so that, periodically, calibration gas is run through the system for maximum accuracy when analyzing a gas stream for an unknown amount of water.

Figure 3:
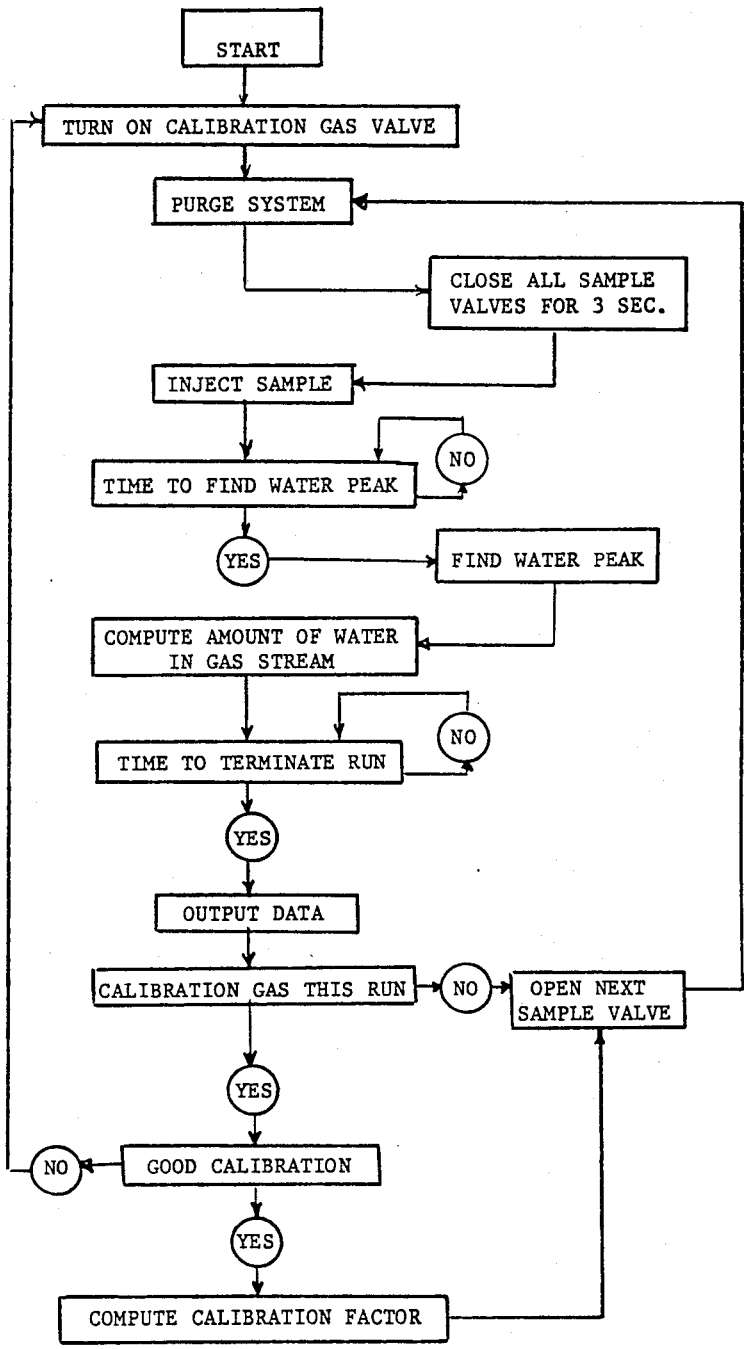
FIG. 3 is a schematic view illustrating the microcomputer control logic.

The micro-computer control logic of the invention is depicted in schematic form in FIG. 3. The control logic of FIG. 3 permits the various functions described hereinabove to be performed.

Thus it can be seen that a method has been provided for automatically measuring the amount of water in a natural gas pipeline with the aid of a computer control gas chromatograph. The method described herein permits the detection and measurement of low water levels in gaseous hydrocarbons flowing in a pipeline. Thus it can been seen that the method accomplishes at least all of the stated objectives.

I claim:

1. A method for automatically measuring low water levels in a natural gas pipeline with the aid of an electron capture gas chromatograph selectively fluidly connected to the natural gas pipeline and a computer control unit, comprising the steps of: providing said computer control unit with a data base for operating said electron capture gas chromatograph, the data base capable of at least,
  (a) periodically causing a sample of the natural gas to be supplied to said gas chromatograph;
  (b) operating said gas chromatograph to measure the water in said natural gas;
  (c) computing the amount of said water in said natural gas; and
  (d) reporting the amount of said water in said natural gas.

* * * * *